(12) United States Patent
Weiss

(10) Patent No.: US 6,358,748 B1
(45) Date of Patent: Mar. 19, 2002

(54) MICROBEND FIBER-OPTIC CHEMICAL SENSOR

(75) Inventor: Jonathan D. Weiss, Albuquerque, NM (US)

(73) Assignee: The United States of America as represented by the U.S. Department of Energy, Washington, DC (US)

(*) Notice: Subject to any disclaimer, the term of this patent is extended or adjusted under 35 U.S.C. 154(b) by 0 days.

(21) Appl. No.: 09/677,611

(22) Filed: Sep. 28, 2000

(51) Int. Cl.[7] ............................................... G01N 21/64
(52) U.S. Cl. .................. 436/172; 422/82.08; 422/82.11
(58) Field of Search ........................... 422/82.05, 82.06, 422/82.07, 82.08, 82.11; 436/172; 250/456.1, 459.1

(56) References Cited

U.S. PATENT DOCUMENTS

| | | | | |
|---|---|---|---|---|
| 4,870,292 A | * | 9/1989 | Alpert et al. ................ 250/577 |
| 5,061,857 A | * | 10/1991 | Thompson et al. ....... 250/458.1 |
| 5,082,629 A | * | 1/1992 | Burgess, Jr. et al. ..... 422/82.11 |
| 5,132,529 A | | 7/1992 | Weiss ..................... 250/227.16 |
| 5,195,162 A | * | 3/1993 | Sultan et al. ................ 385/130 |
| 5,260,566 A | * | 11/1993 | Reed ...................... 250/277.16 |
| 5,928,222 A | * | 7/1999 | Kleinerman .................. 606/16 |
| 5,991,479 A | * | 11/1999 | Kleinerman .................. 385/31 |
| 6,013,532 A | * | 8/2000 | Koch et al. .................... 436/55 |
| 6,289,144 B1 | * | 9/2001 | Neuschafer et al. .......... 385/12 |

OTHER PUBLICATIONS

J. Weiss, "Fiber–Optic Strain Gauge," *Journal of Lightwave Technology*, vol. 7, No. 9, pp. 1308–1318 (Sep. 1989).
B. MacGraith, et al., "Fibre Optic Fluorescence Sensors Based On Sol–Gel Entrapped Dyes", *Proceedings of the European Congress on Optics*, SPIE vol. 1510, Chemical and Medical Sensors, pp. 104–109 (Mar. 1991).

* cited by examiner

*Primary Examiner*—Jeffrey Snay
(74) *Attorney, Agent, or Firm*—James C. Durkis; Dickson G. Kehl; Virginia B. Caress

(57) ABSTRACT

A microbend fiber-optic chemical sensor for detecting chemicals in a sample, and a method for its use, is disclosed. The sensor comprises at least one optical fiber having a microbend section (a section of small undulations in its axis), for transmitting and receiving light. In transmission, light guided through the microbend section scatters out of the fiber core and interacts, either directly or indirectly, with the chemical in the sample, inducing fluorescence radiation. Fluorescence radiation is scattered back into the microbend section and returned to an optical detector for determining characteristics of the fluorescence radiation quantifying the presence of a specific chemical.

37 Claims, 5 Drawing Sheets

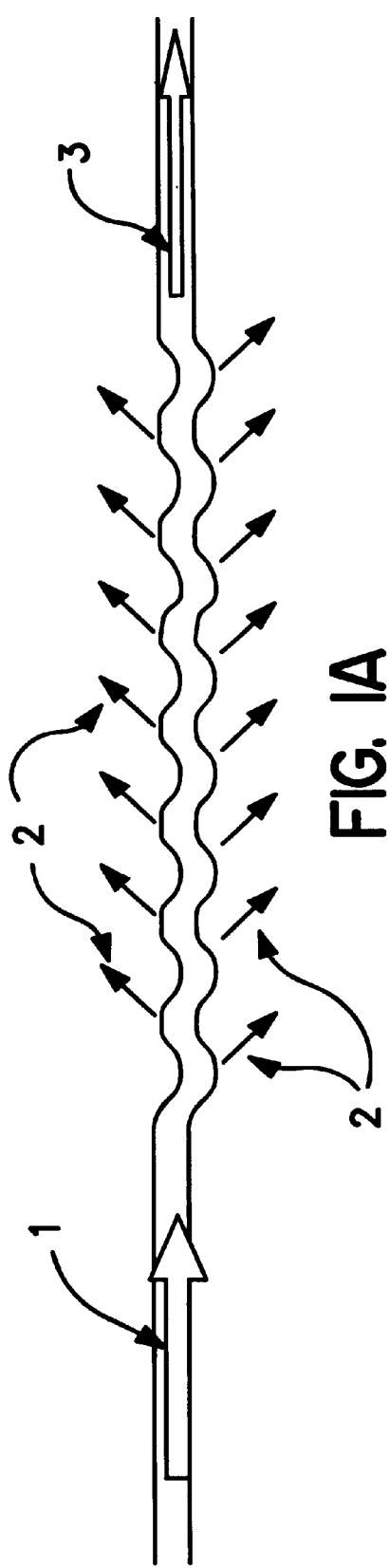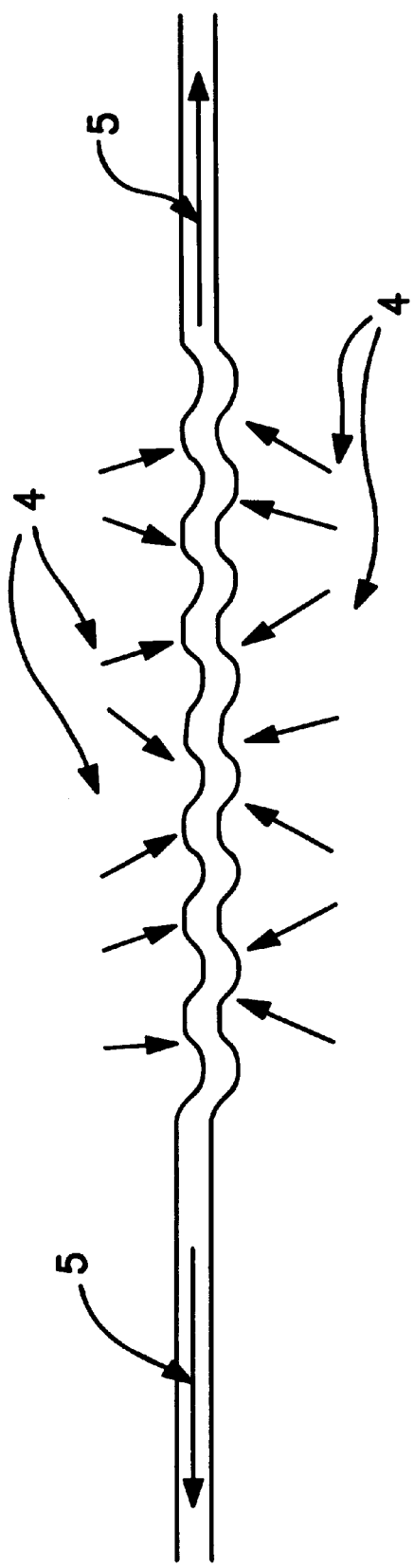
FIG. IA
FIG. IB

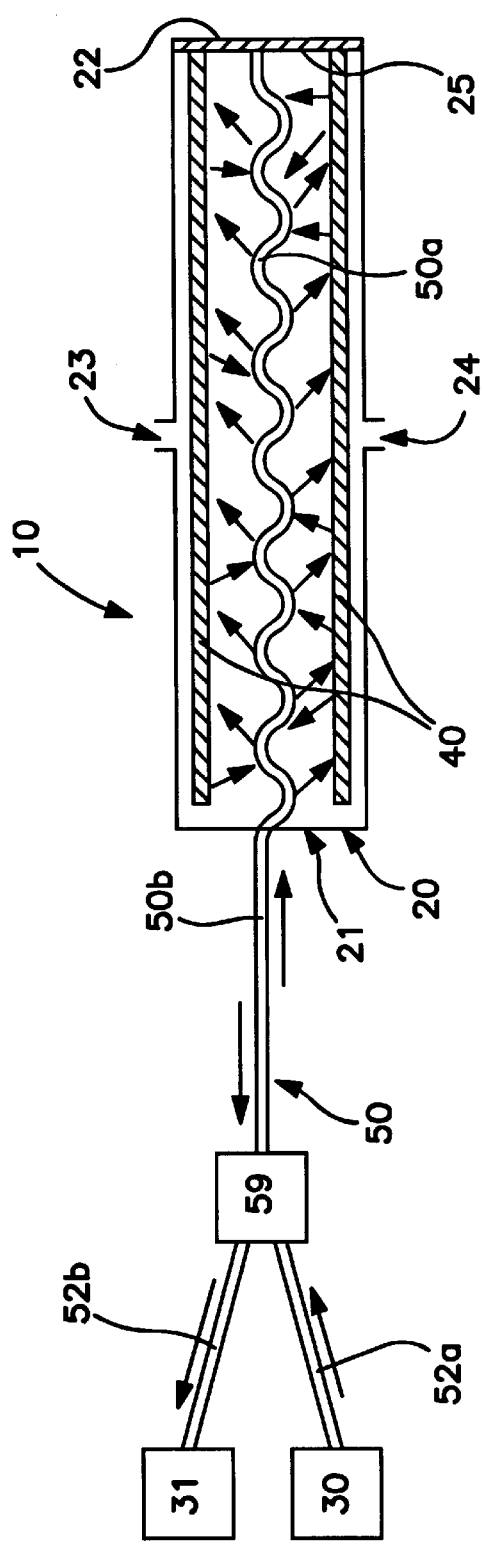
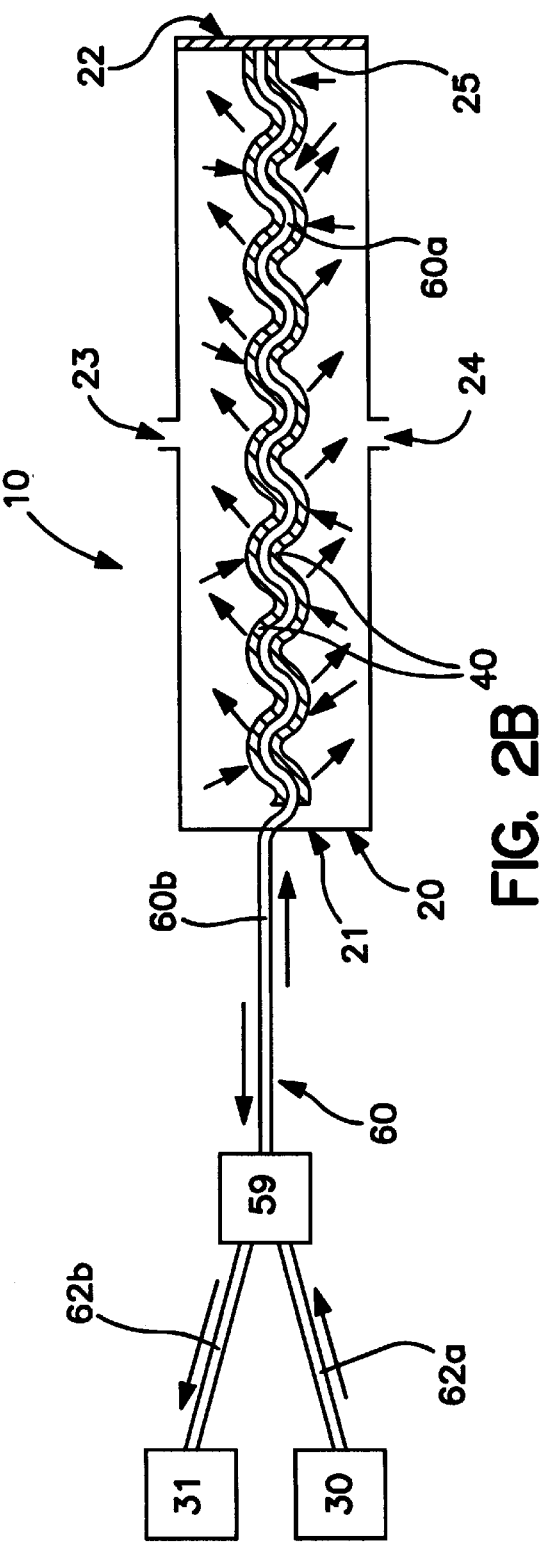
FIG. 2A
FIG. 2B

MICROBEND FIBER-OPTIC CHEMICAL SENSOR

The present invention was conceived and developed under U.S. Government Contract No. DE-AC04-94AL85000 awarded by the U.S. Department of Energy. The Government has rights in this invention.

FIELD OF THE INVENTION

The present invention relates to chemical sensors, particularly a microbend fiber-optic chemical sensor adapted to detect certain chemical species.

BACKGROUND OF THE INVENTION

Chemical detection is a necessity for many applications. Most chemical sensors currently used are electrical. While performing adequately in many applications, they are susceptible to electromagnetic interference and can cause unacceptable sparking in potentially explosive environments.

The development of fiber-optic technology and the application of the fiber-optic technology to chemical sensors has permitted construction of chemical sensors with at least two advantages over their electrical counterparts: immunity to electromagnetic interference and safe performance in a potentially explosive environment. Furthermore, the geometric flexibility of optical fibers and their ability to confine light allow for remote measurement in chemically aggressive environments.

However, existing fiber-optic chemical sensors require modification of at least one constituent, and frequently involve removing an original cladding over certain sections of the fiber and replacing it with cladding that reacts with the chemical compositions being monitored. This reaction can produce an absorptive cladding and thus attenuated total internal reflection, or a change in a cladding reflective index and thus reduced guidance, particularly if the light is sent into the optic fiber off-axis. The reaction can also modify the cladding so as to enhance or suppress fluorescence generated within it when "pump" light is sent through the fiber.

Known fiber-optic chemical sensors can also have sensitivity problems, either because the reaction does not strongly modify the cladding or because only a small fraction of the fluorescence is coupled into the guided modes of the fiber. In addition, these modifications require careful post-processing of the fiber.

There is a current need for a fiber-optic chemical sensor that will not require modification of its constituents or alteration of the cladding and that avoids the sensitivity problems of known fiber-optic chemical sensors.

U.S. Pat. No. 5,132,539, dated Jul. 21, 1992, to Jonathan E. Weiss, discloses a microbend fiber-optic strain sensor that relies on permanent microbends, impressed in a 254-micron plastic optical fiber, to induce optical scattering out of the fiber core. The patented strain sensor relied on the fact that tension in the fiber caused "out-scattering" to rapidly diminish through the unfolding of the microbends.

SUMMARY OF THE INVENTION

The present invention solves the problems typical of known fiber-optic chemical sensors. According to the present invention, there is provided a microbend fiber-optic chemical sensor for detecting certain predetermined chemicals in a chemical-bearing liquid or gas, by detecting a change in the characteristics of fluorescent light conducted through optical fibers, and a method for its use. Unlike known fiber-optic chemical sensors, no removal of the cladding and re-coating of the fiber are necessary in the present invention.

Unlike the previously described, patented strain sensor, the present invention relies on both "out-scattering" and "in-scattering", and does not rely on strain. In the present invention, all fibers are relaxed so that no thermally-induced changes in tension occur.

The microbend fiber-optic chemical sensor of the present invention comprises at least one optical fiber, having a microbend section (a section comprising small undulations in the axis of the fiber(s)), for transmitting and receiving light. In the transmission phase, pump light is sent through the microbend section of the optical fiber(s), where the microbends cause optical scattering of the pump light out of the fiber core. In the receiving phase, changed fluorescent radiation resulting from the interaction of the light with the chemical, either directly or indirectly, is scattered into the microbend section of the optical fiber(s) and is then conducted by the fiber(s) to an optical detector.

In one embodiment, the analyte is "pumped" directly with light that is out-scattered from the optical fiber(s) in the transmitting phase. The out-scattered light excites fluorescence radiation in the chemical species to be detected, and the fluorescence radiation characteristic of the particular molecular species "in-scatters" into the fiber(s), in the receiving phase, and travels to a detector where the intensity of the light, indicative of the concentration of the species, is detected.

In alternative embodiments, the microbend fiber-optic chemical sensor of the present invention comprises a fluorescer-bearing membrane in interactive contact with the transmitting and receiving optical fiber(s). The fluorescer-bearing membrane is structurally formed either as a separate structure or a coating of the fiber(s) of the sensor, in either case remaining in interactive contact with the optical fiber(s) of the sensor.

Where the microbend fiber-optic chemical sensor comprises a fluorescer-bearing membrane, the fluorescent material of the membrane interacts with the specific chemical or chemicals to be detected. Upon contact with the fluorescer-bearing membrane, the pump light scattered out of the fiber(s) induces fluorescence radiation, and the interaction between the fluorescers of the membrane and the chemical changes various fluorescence characteristics of the fluorescence radiation induced by the contact. The changed fluorescence radiation is then in-scattered to the optical fiber(s) in the receiving phase, and travels to a detector where the nature of the changes determine the presence and other characteristics of the chemical.

The exact nature of the change in fluorescence radiation depends on the chemical to be identified. The fluorescence radiation is enhanced or quenched, depending on the chemical in the sample, causing increase or reduction, respectively, in its optical power and, therefore, in the signal that goes to the detector. When the changed optical power is detected, the presence (and other characteristics) of the specific chemical can be determined. The change in the fluorescence radiation may also be reflected by a shift or change in shape in its fluorescence spectrum, in which case spectral analysis is used to detect the chemical.

Additional objects, advantages and novel features, and further scope of applicability of the present invention will be set forth in part in the detailed description to follow, taken in conjunction with the accompanying figures, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the operation, features, and advantages of the invention. The drawings are only for the purpose of illustrating certain embodiments of the invention and are not to be construed as limiting the invention. In the drawings:

FIG. 1A illustrates the process of optical scattering out of a fiber core of light guided through a microbend section of an optical fiber.

FIG. 1B illustrates the process of optical scattering into a fiber core of light irradiating a microbend section of an optical fiber.

FIG. 2A illustrates the microbend fiber-optic chemical sensor in cross-section, with one optical fiber for transmitting and receiving light with a fluorescer-bearing membrane surrounding the optical fiber.

FIG. 2B illustrates the microbend fiber-optic chemical sensor in cross-section, with one optical fiber for transmitting and receiving light with the fluorescer-bearing membrane coated on the optical fiber.

DETAILED DESCRIPTION OF THE INVENTION

Figure 3A:
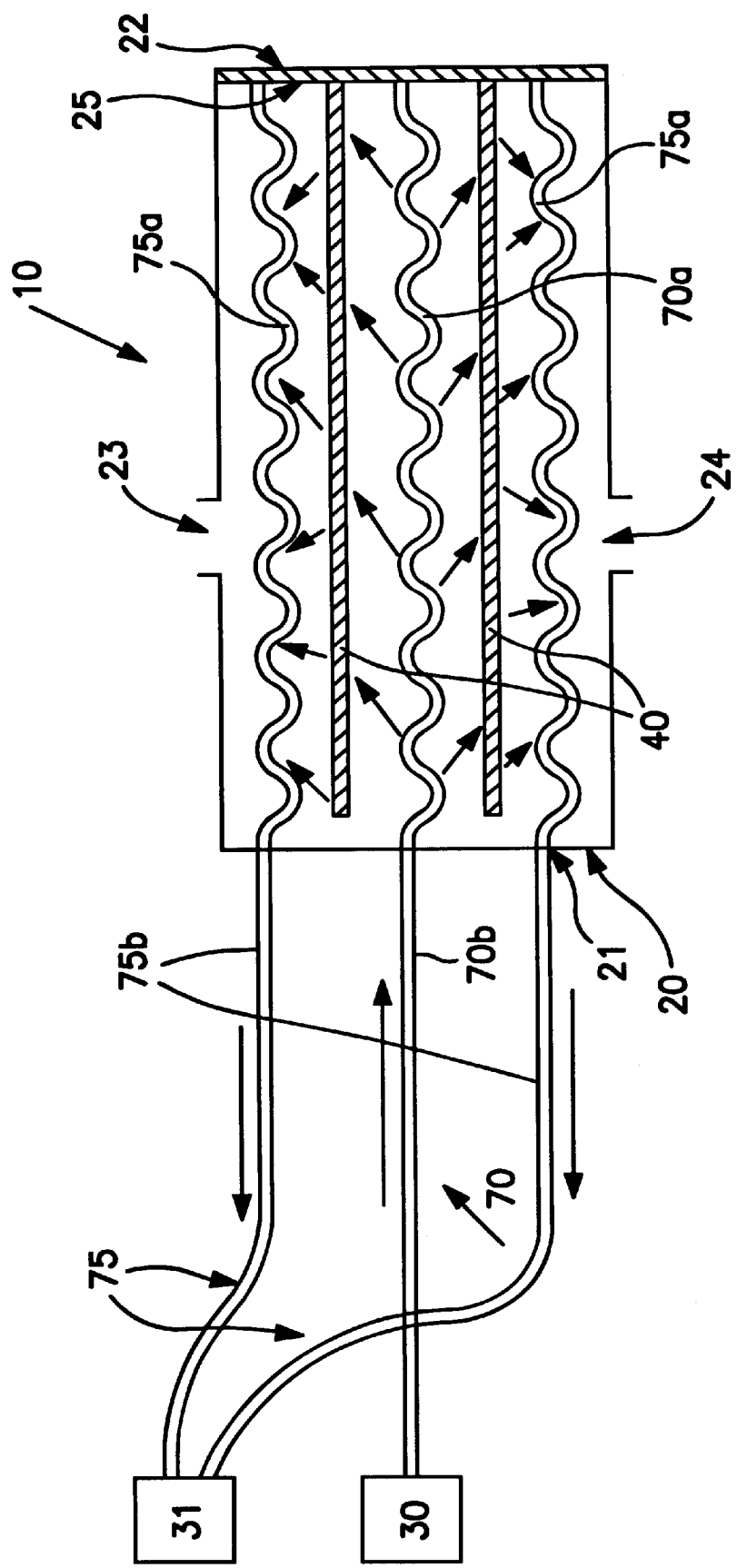
FIG. 3A illustrates the microbend fiber-optic chemical sensor in cross-section, with two optical fibers with a fluorescer-bearing membrane surrounding the optical fibers.

A microbend fiber-optic chemical sensor for detecting certain chemicals, such as chlorine and oxides of nitrogen (e.g., nitrogen dioxide), and a method for its operation, are disclosed. The microbend fiber-optic chemical sensor of the present invention comprises one or more optical fibers containing microbends, i.e., random or periodic undulations in the axis of the optical fiber. For the purposes of the general description of the microbend fiber-optic chemical sensor, since the optical fibers can be either single or multiple, where appropriate, they will be described as "optical fiber (s)" or "fiber(s)" except with respect to particular embodiments or Figures.

Microbends are typically small in amplitude compared to the diameter of the optical fiber. Microbends cause optical scattering out of the optical fiber core, when light is transmitted through the fiber. This basic out-scattering process is illustrated in FIG. 1A, where light enters the optical fiber at 1, is scattered out of the microbend section at 2 and exits the fiber at 3.

In addition to the scattering of light out of the optical fiber core, microbends, when illuminated with light, cause light to be scattered into the fiber. This in-scattering process is illustrated in FIG. 1B, where laterally incident light enters the optical fiber at the microbend section at 4 and exits the optical fiber at both ends (on either side of the microbend section) at 5. Both out-scattering and in-scattering have been observed and various uses for the out-scattering phenomenon are known. However, the utility of the in-scattering function for chemical detection has been newly discovered in the present invention.

The microbend fiber-optic chemical sensor of the present invention comprises at least one optical fiber, comprising both a microbend section and a straight section, for "pump" transmitting light and receiving light, i.e., for both out-scattering and in-scattering. The actual number of transmitting/receiving optical fiber(s) is not fixed: the sensor can include any number of optical fibers either for transmitting or for receiving light, that is, there may be multiple transmitting fibers as well as multiple receiving fibers. Likewise, the sensor may include different numbers of transmitting fibers than receiving fibers; it is not restricted to comprising more or less transmitting fibers than receiving fibers. The use of more fibers adds to the efficiency of the sensor, but the choice of the actual number is largely a matter of the geometry that must be chosen to gain the desired efficiency.

Each fiber used must comprise a microbend section and a straight section. The arrangement of a bundle of transmitting and receiving fibers, relative to each other, is also not fixed. For instance, in embodiments with one transmitting fiber and multiple receiving fibers, such as will be shown in three of the embodiments described herein, the transmitting fiber need not be disposed in the middle surrounded by the receiving fibers, although the multiple-fiber embodiments described herein are shown with the fibers in that arrangement for easier depiction. Also, the respective microbend sections of multiple fibers can be disposed adjacent to each other or staggered (longitudinally displaced) in the sensor. However, the fibers of multiple-fiber embodiments are parallel in any case. The microbend radiation is concentrated preferentially in the plane of the bends in the fiber(s). In-scattering is more efficient when the radiation is traveling parallel to the plane of the bends than perpendicular to it.

The method of use for any of the embodiments of the microbend fiber-optic chemical sensor begins with the transmission of "pump" light. "Pump" light is sent through the fiber or fibers of the microbend fiber-optic chemical sensor. "Pump" light is defined for the purposes of this invention as light that excites fluorescence from the material it interacts with (i.e., it causes interactive material to emit its own radiation (fluorescence radiation)). The source of the pump light is in operative contact with the transmitting optical fiber or fibers; the receiving fiber or fibers are not in operative contact with the pump source. The pump light source is not necessarily in physical contact with the fiber(s), although it can be.

In the embodiment most closely represented by FIGS. 1A and 1B, the microbend fiber-optic chemical sensor of the present invention comprises one optical fiber having a microbend section and a straight section, and the analyte is pumped directly with light out-scattered from the optical fiber in the transmitting phase; this light excites fluorescence radiation from the analyte. That is, out-scattered light induces fluorescence in the species to be detected where there was originally no fluorescence. The fluorescence radiation characteristic of the particular molecular species "in-scatters" into the fiber, in the receiving phase, and travels to a detector where the intensity of the light is related to the concentration of the species in question (i.e., intensity is detected). If two or more chemical species are present simultaneously in the sample, and if significant overlap between their respective fluorescence spectra exists, then a spectroscopic analysis of the light may be necessary to quantify their respective concentrations.

When it is not efficient or practical to pump the analyte directly, the microbend fiber-optic chemical sensor of the present invention further comprises a fluorescer bearing membrane to facilitate the reaction. In the embodiments to be described herein, the fluorescer-bearing membrane is either a separate structure surrounding the fiber(s) or a coating applied to the fiber(s). The fluorescer-bearing membrane is desirable in a number of situations: when the fluorescence efficiency of the species itself is low; when the species does not fluoresce in a convenient region of the electromagnetic spectrum (convenience here is defined in terms of how well the chosen optical fiber(s) transmit the light or how efficient the chosen detector is); or when an inconvenient pump wavelength is required (convenience here is defined in terms of how well the chosen fiber(s) transmit the light, or how inexpensive, compact, or commercially available the "pump" light source is).

In accordance with the invention, the fluorescer-bearing membrane contains fluorescers, a chemically sensitive fluorescent composition or material that interacts with the chemical to be detected. The membrane is designed to react selectively with the known chemical, i.e., the fluorescers chosen for the membrane are selective for the chemical being tested in the sample. The fluorescer-bearing membrane is placed into interactive contact with (adjacent to) the microbend sections of the optical fiber or fibers included in the sensor, such that pump light out-scattering from the optical fiber(s) in the transmitting phase induces fluorescence radiation upon contact with the membrane.

In operation, where the microbend fiber-optic chemical sensor comprises a fluorescer-bearing membrane, the in-scattering light 4 of FIG. 1B derives from the fluorescence (or lack thereof) coming from the fluorescer-bearing membrane. Pump light transmitted along the fiber or fibers of the microbend fiber-optic chemical sensor out-scatters from the microbend section, contacts the fluorescer-bearing membrane and excites the fluorescers of the membrane to radiate or to fluoresce (to emit its own radiation (fluorescence radiation)). The fluorescers in the membrane are also interacting with the chemical, not necessarily because of the light. Changes in the induced fluorescence radiation occur when the light contacts the fluorescer-bearing membrane in the presence of the specific, known chemical or chemicals to be identified, i.e. the reaction between the fluorescers and the chemical changes the fluorescence characteristics of the induced fluorescence radiation (as expected due to the chemical being sought). The changed fluorescence radiation is then in-scattered into the optical fiber(s) in the receiving phase.

The exact nature of the change in fluorescence depends on the characteristics of the chemical to be identified in the sample being tested. As a result of the change in fluorescence characteristics, the optical power of the light scattered out of the membrane changes accordingly. The optical power of the light being conducted by the fiber(s) is quenched or enhanced as the fluorescence radiation produced by the membrane is quenched or enhanced, and the signal picked up by the detector is also changed accordingly.

Also, the interaction between the membrane and the chemical shifts the spectral content of the fluorescence radiation in wavelength, thus changing the shape of its fluorescence spectrum. When a shift or change in the spectrum is to be detected, spectral analysis can be used for detection of the chemical. As an example of the use of spectral analysis, blue light is transmitted into the membrane, which fluoresces in the red resulting in a spectrum shift down or up or a change in the spectrum shape. A spectrometer is used to "see" the spectrum and how much light lies at what wavelength. The result is seen independent of intensity and is therefore more accurate without the influence of intensity changes in incoming light. This type of analysis searches for the position of the peak rather than a change in signal. As another example, in detecting the shift, a ratio can be taken of the signal at three different wavelengths, as a function of the spectrum of the fluorescent signal. The ratio is insensitive to the overall intensity of the light; therefore fewer controls are required in the system to screen out extraneous confounders or "noise".

FIGS. 2A, 2B, 3A and 3B depict the microbend fiber-optic chemical sensor 10 in cross-section, in accordance with different embodiments of the present invention. The distinctions between these embodiments of the sensor of the invention are directed to the structural relationship of the optical fiber(s) and the fluorescer-bearing membrane depicted in each of these Figures.

In each of FIGS. 2A, 2B, 3A and 3B, microbend fiber-optic chemical sensor 10 comprises a housing 20 having a first end 21 and a second end 22. Housing 20 comprises an inlet port 23 and an outlet port 24 for entry, circulation, and exit of the chemical-bearing fluid (liquid or gas) through the sensor. Housing 20 further comprises a light-reflecting surface 25 at the second end 22. Housing 20 can be of any appropriate shape, such cylindrical, rectangular, etc. Additionally, although light-reflecting surface 25 is depicted in the embodiments described herein as being located at second end 22 of the housing, the choice of location and shape of light-reflecting surface 25 is directed to returning as much light as possible back to the fiber(s). For instance, it is contemplated that a light-reflecting surface 25 can extend lengthwise along the interior surface of the housing parallel to the arrangement of the optical fiber(s). Although this arrangement operates as does the structure depicted in the Figures, the greater coverage allowed by a lengthwise disposition of light-reflecting surface 25 provides more efficiency, more light is captured by the fibers.

Whether single or multiple, in each of the embodiments shown in FIGS. 2A, 2B, 3A and 3B, the optical fiber(s) shown include a microbend section (denoted a) and a straight section (denoted b), and microbend section a of the fiber(s) is arranged in interactive contact with fluorescer-bearing membrane 40. In each of these embodiments, the microbend section(s) a of the optical fiber(s) include at least one random or periodic undulation in the axis of the optical fiber, as shown previously in FIGS. 1A and 1B. In each of these embodiments, the microbend section a of the fiber(s) and the associated fluorescer-bearing membrane 40 are disposed within the housing 20. In each of these embodiments, also, a proximal end of the straight section b of the optical fiber(s) is coupled to a source of pump light 30 and an optical detector 31, both pump light source 30 and optical detector 31 being located outside of housing 20. Also, in each of these embodiments, an end face of a distal end (or far end) of the microbend section a abuts the light-reflecting surface 25 contained in housing 20 in interactive contact. This contact is typically maintained by coupling the fiber to surface 25 by bonding; however, any appropriate procedure for maintenance of the contact can be employed.

Finally, in each of the embodiments, an optical filter (not shown) can be positioned between the microbend section a of the optical fiber(s) and detector 31, in order to prevent pump light from introducing errors into the measurement. It is desirable that light coming into the receiving fiber(s) from the fluorescer-bearing membrane 40 be fluorescent light and not pump light. To prevent pump light that gets into the receiving fiber(s) from being detected and thus causing error in the signal, the optical filter is placed in front of detector 31 to filter out pump light.

The method of operation for each of the embodiments comprises flooding housing 20 with liquid or gas sample thought to contain a one or more predetermined known chemical species. The chemical-bearing liquid or gas passes through the housing by means of inlet port 23 and an outlet port 24. In order to detect the specific chemical species, pump light from source 30 is sent through the optical fiber(s). In the transmitting phase, at microbend section a, the pump light causes optical scattering out of the fiber(s) due to the microbends. The light scattered out of the microbend section a of the optical fiber(s) irradiates the fluorescer-bearing membrane 40 and induces fluorescence therein. When the chemically sensitive fluorescent composition of the fluorescer-bearing membrane 40 interacts with the chemical species to be detected in the presence of the out-scattered light, the fluorescence of the membrane is quenched or enhanced or the fluorescence spectrum of the membrane 40 shifts, as previously described.

Inside housing 20, after light travels the length of microbend section a, it contacts light-reflecting surface 25 disposed inside housing 20 at the end of microbend section a. Light-reflecting surface 25 scatters out the pump light that was not scattered out through the first pass and re-directs the captured fluorescent radiation that originally traveled away from the optical detector 31 back toward detector 31. In the receiving phase, the fluorescent radiation from the fluorescer-bearing membrane 40 is scattered back into the microbend section a ("in-scattering") and transmitted to optical detector 31.

If a change in the optical power of the light conducted from the microbend section a of the optical fiber(s) inside housing 20 and through the light-receiving straight section b of the optical fiber(s) outside housing 20 is detected by the optical detector 31, the presence, concentration and amount of the specific chemical species is determined. Also, as previously described, the shift in spectrum may be analyzed by spectral analysis to determining characteristics of the chemical being identified, e.g., concentration.

The embodiments shown in FIGS. 2A, 2B, 3A, and 3B differ from each other in the number and arrangement of optical fibers in relation to the fluorescer-bearing membrane. FIGS. 2A and 2B depict the microbend fiber-optic chemical sensor 10 of the present invention in embodiments with a single optical fiber for both pump transmitting light and receiving light (for both out-scattering and in-scattering). The use of a single optical fiber has the advantage of providing a more compact microbend fiber-optic chemical sensor, however, it requires, as an additional feature, a splitter 59 between the fiber and source 30 and detector 31 to separate transmitted from received light. The splitter causes approximately a 50% loss in both pump and fluorescence radiation. In addition, with only one fiber, the signal from the transmitted and received light cannot be separately optimized to provide only transmitting or receiving functions. If both functions are provided by one fiber, there must be some compromise to provide both functions, meaning a reduction in the overall signal as compared to the embodiments with multiple fibers.

FIG. 2A shows optical fiber 50 including a microbend section 50a disposed within housing 20 and a straight section 50b disposed outside of housing 20. A proximal (near) end of the straight section 50b is split to allow it to couple to pump light source 30 and optical detector 31 by means of splitter 59 through a light-guiding optical fiber 52a and a light-receiving optical fiber 52b. Distal (far) end of microbend section 50a is coupled to light-reflecting surface 25. In FIG. 2A, fluorescer-bearing membrane 40 (shown in cross-section) surrounds, but is spaced apart from, microbend section 50a of optical fiber 50. Advantageously, when membrane 40 is separate from the fiber(s), its design and placement can be optimized for interaction with both pump and receiving fiber(s). Additionally, more surface area is exposed to pump radiation and to the chemical when membrane 40 is a separate structure from the fiber(s).

FIG. 2B also depicts the microbend fiber-optic chemical sensor 10 having a single optical fiber 60 for both pump light and receiving light (for both out-scattering and in-scattering). FIG. 2B is the most compact of the embodiments of the microbend fiber-optic chemical sensor described herein. The optical fiber 60 includes a microbend section 60a disposed within housing 20 and a straight section 60b outside of housing 20. A proximal (near) end of the straight section 60b is split to allow it to couple to pump light source 30 and detector 31 by means of splitter 59 through light-guiding optical fiber 62a and light-receiving optical fiber 62b. Distal (far) end of microbend section 60a is coupled to light-reflecting surface 25. In FIG. 2B, microbend section 60a of the optical fiber 60 is coated with fluorescer-bearing material 40 (still shown in cross-section) over its cladding layer. In cases where the sensor is a single-fiber sensor, coating the fiber has the advantage of preventing any divergence of the pump radiation to occur before interaction (the pump light hits fiber immediately), i.e., proximity contributes to efficiency although less surface area is exposed to radiation when the membrane is coated on the fiber(s).

Figure 3B:
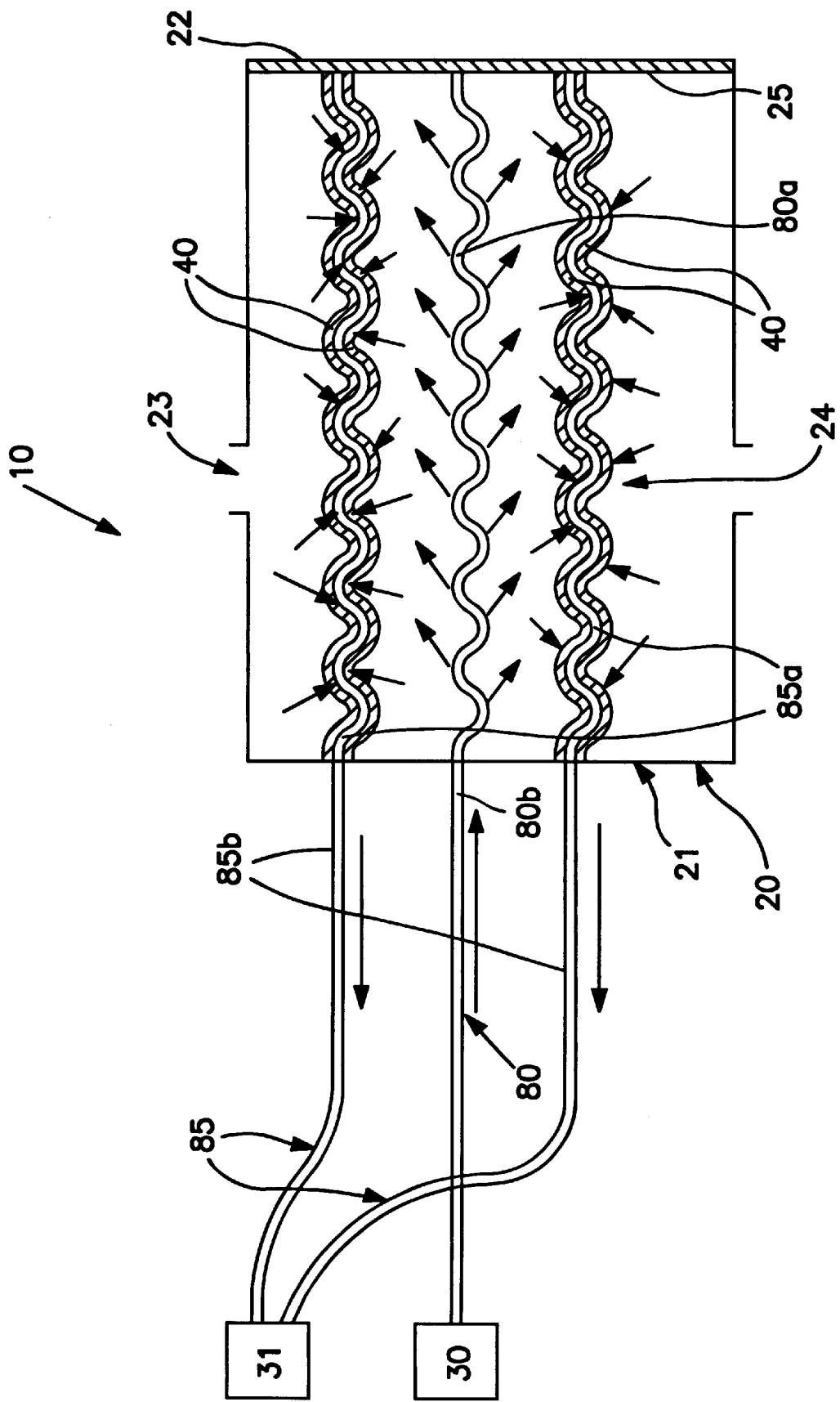
FIG. 3B illustrates the microbend fiber-optic chemical sensor in cross-section, with two optical fibers with the fluorescer-bearing membrane coated on the optical fibers.

FIGS. 3A and 3B depict microbend fiber-optic chemical sensor 10 in embodiments having separate optical fibers for pump transmitting light and receiving light, as shown, one optical fiber for transmitting light and more than one for receiving light. Using multiple optical fibers in the microbend fiber-optic chemical sensor 10 is advantageous in that more flexibility is attained in terms of optimizing the design, e.g., the location, of membrane 40 for increased interaction with the transmitting and receiving fibers, and the signal, e.g., each fiber can be optimized separately for its respective function. Also, unlike the embodiments of FIGS. 2A and 2B, in the embodiments of FIGS. 3A and 3B, no splitter is necessary to separate transmitted from received light.

The microbend fiber-optic chemical sensor 10 in accordance with FIG. 3A comprises one transmitting optical fiber 70, and two receiving optical fibers 75, and a fluorescer-bearing membrane 40, surrounding but separate from fibers 70 and 75. The transmitting optical fiber 70 includes a microbend section 70a and a straight section 70b. Correspondingly, each of the receiving optical fibers 75 includes a microbend section 75a and a straight section 75b. Microbend sections 70a and 75a are disposed inside housing 20. Straight sections 70b and 75b are disposed outside housing 20. Fluorescer-bearing membrane 40 is also disposed within housing 20 in interactive relationship with microbend sections 70a and 75a.

As seen in FIG. 3A, microbend section 70a of transmitting fiber 70 is located between microbend sections 75a of receiving fibers 75 and is spaced apart therefrom. A proximal (near) end of transmitting fiber 70b is coupled to pump light source 30. Correspondingly, proximal ends of the receiving fibers 75b are coupled to optical detector 31. As in FIGS. 2A and 2B, in FIG. 3A, distal (far) ends of the microbend sections 70a and 75a of transmitting fiber 70 and receiving fibers 75 are coupled to light-reflecting surface 25 inside housing 20. Fluorescer-bearing membrane 40, shown in cross-section, is a separate structure from transmitting fiber 70 and receiving fibers 75. Membrane 40 surrounds microbend section 70a of transmitting fiber 70; microbend sections 75a of receiving fibers 75 are disposed outside the "tube" formed by membrane 40, such that membrane 40 lies between transmitting fiber 70 and receiving fibers 75.

In accordance with another embodiment of the present invention, illustrated in FIG. 3B, microbend fiber-optic chemical sensor 10 comprises a transmitting optical fiber 80 and two receiving optical fibers 85. Transmitting optical fiber 80 includes a microbend section 80a and a straight section 80b. Correspondingly, each of receiving optical fibers 85 includes a microbend section 85a and a straight section 85b. Microbend sections 80a and 85a are disposed within housing 20; straight sections 80b and 85b are disposed outside housing 20.

As seen in FIG. 3B, microbend section 80a of the transmitting fiber 80 is located between microbend sections 85a of the receiving fibers 85, and is spaced apart therefrom. A proximal (near) end of the transmitting fiber 80b is coupled to pump light source 30. Correspondingly, proximal ends of the receiving fibers 85b are coupled to optical detector 31. As in FIGS. 2A, 2B and 3A, in FIG. 3B, distal (far) ends of the microbend sections of transmitting fiber 80a and receiving fibers 85a are coupled to light-reflecting surface 25. In this embodiment, microbend sections 85a of the receiving fibers 85 are coated with fluorescer-bearing membrane 40; note that for practicality, when there are separate transmitting and receiving fibers, the transmitting fiber is not coated.

The method of using embodiments of the microbend fiber-optic chemical sensor comprising more than one optical fiber for transmitting and receiving is approximately the same as the method of using embodiments comprising only one optical fiber for transmitting and receiving. In order to detect the predetermined chemical species, pump light from the source 30 is sent through the transmitting optical fibers 50 (FIG. 2A), 60 (FIG. 2B), 70 (FIG. 3A) and 80 (FIG. 3B), respectively. In the microbend sections 50a (FIG. 2A), 60a (FIG. 2B), 70a (FIG. 3A) and 80a (FIG. 3B), pump light causes optical scattering out of the respective fibers. Light scattered out of the microbend sections a, respectively, irradiates fluorescer-bearing membrane 40, whether formed as a separate structure or a coating, thus inducing fluorescence. The fluorescent radiation from fluorescer-bearing membrane 40 is changed by contact with the interaction between membrane 40 and the chemical in the sample and scattered back into the microbend sections 50a and 60a of the FIGS. 2A and 2B, respectively (the single-fiber embodiments), and enters microbend sections 75a and 85a of receiving optical fibers 75 and 85 of FIGS. FIGS. 3A and 3B, respectively (the multiple fiber embodiments). Whether the embodiment comprises single or multiple fibers, in-scattered fluorescence radiation is returned to optical detector 31. Again, the interaction of fluorescer-bearing membrane 40 with the chemical species to be detected quenches or enhances the fluorescence radiation of the membrane according to the chemical composition of the fluorescer-bearing membrane, which changes likewise the fluorescence characteristics, e.g., optical power, of the radiation traveling to detector 31. If a change in the optical power of the light conducted through the receiving optical fiber is detected by optical detector 31, the presence and/or amount of the specific chemical species is determined. Alternatively, as previously described, a shift in the fluoresence spectrum can be detected and analyzed by a spectrometer.

Where the microbend fiber-optic chemical sensor incorporates a fluorescer-bearing membrane, the fibers, either transmitting or receiving, need not touch or actually contact the membrane or the chemical, if it is expected that the chemical(s) in the membrane or the chemical to be detected might be corrosive or otherwise damaging to the fibers. The chemical to be identified must contact the fluorescer-bearing membrane, but can be prevented from physically contacting the fiber, which is advantageous in that the need for structure to prevent potentially damaging contact is eliminated. Segregation of the fiber(s) from the chemical can also be accomplished structurally, e.g., a protective barrier transparent to light. Where the fibers of the microbend fiber-optic chemical sensor queries the analyte directly and no fluorescer-bearing membrane is incorporated, the analyte, if corrosive, can be retained outside housing 20, which acts as a protective housing in these circumstances.

The surfaces of fluorescer-bearing membrane 40 can be curved or planar or of any other appropriate shape that will interact as desired with microbend section(s) a of the optical fiber(s) (whether single or multiple) used in microbend fiber-optic chemical sensor 10. The design and geometry (i.e., shape) of membrane 40 are chosen to optimize the signal, i.e., to provide as much fluorescent power or light as possible. As an example, fluorescer-bearing membrane 40 can be a hollow cylindrical member (shown as a tube) enclosing the microbend sections a of both the transmitting fiber and the receiving fiber(s).

Figure 4:
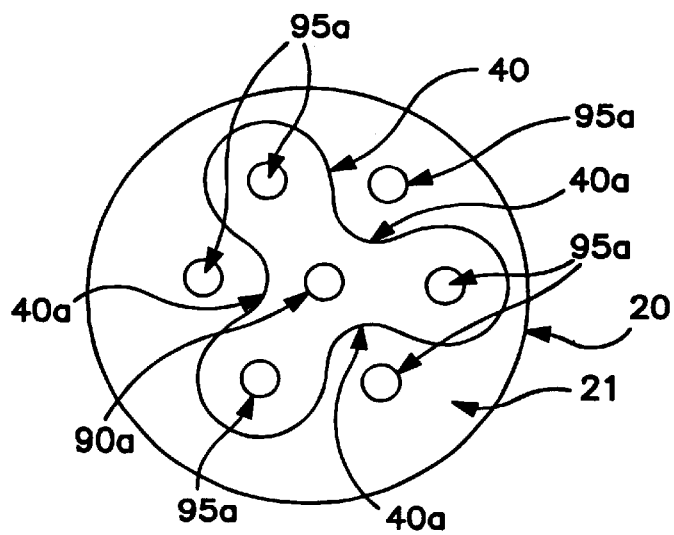
FIG. 4 illustrates an end view of the microbend fiber-optic chemical sensor in cross-section, with a continuous, curved fluorescer-bearing membrane and incorporating multiple optical fibers.

FIG. 4 depicts yet another embodiment of the invention, shown from the first end 21 of the housing 20. In FIG. 4, housing 20 is a hollow tube and fluorescer-bearing membrane 40 is a hollow, continuous, curved member (e.g., a tube 40 with curved or corrugated sides disposed inside tubular housing 20). Transmitting fiber 90 and three of the six multiple receiving fibers 95, along with their respective microbend sections 90a and 95a are enclosed inside tube 40. The remaining receiving fibers 95 are disposed outside tube 40 within the inward extending portions 40a of the corrugations of tube 40. The location of the fibers in this embodiments is designed to provide more surface area for increased coupling and efficiency. Microbend sections 90a and 95a and their respective transmitting fiber 90 and receiving fibers 95 are arranged parallel to each other and parallel to the corrugations in tube 40. The corrugated shape of membrane/tube 40 provides the potential for greater coupling between the fluorescence radiation and receiving fibers 95. The liquid or gas analyte containing the chemical to be detected flows through housing 20 inside and/or outside membrane/tube 40, providing more surface area contact with the fluorescer-bearing membrane. Note that, in situations where the chemical to be detected or its carrier fluid is expected to be corrosive, the structure of FIG. 4 can be easily used to provide a protective barrier for the optical fiber(s), with both transmitting fiber 90 and receiving fibers 95 disposed inside tube 40, which is then designed to be transparent to light and is kept empty during operation.

The method of using microbend fiber-optic chemical sensor 10 shown in the FIG. 4 embodiment is essentially the same as that described for the FIGS. 3A and 3B embodiments. Pump light from a source (not shown) is sent through transmitting optical fiber 90 causing optical scattering out of microbend section 90a, irradiating the fluorescer-bearing membrane 40, and causing it to fluoresce. This fluorescence is then scattered into the microbend sections 95a of receiving fibers 95, and ultimately transmitted to the optical detector (not shown). Again, the interaction of fluorescer-bearing membrane 40 with the chemical species to be detected changes the fluorescence of the membrane 40 and thereby the optical power of the light conducted through receiving fibers 95. The change in optical power is detected by the optical detector, and the presence and/or concentration of the specific chemical species is determined. If appropriate, a shift in the fluorescence spectrum can be used to determine the chemical concentration.

In yet another embodiment (not shown), housing 20 of microbend fiber-optic chemical sensor 10 is completely mirrored internally and formed as a tube having an elliptical shape in cross section. Sensor 10 includes at least two optical fibers, at least one for transmitting and at least one for receiving, with fluorescer-bearing membrane 40 formed as a coating on the receiving fiber(s). The transmitting (pump) fiber(s) and receiving fiber(s) are placed at either focus of the ellipse, in any chosen arrangement respectively. Given the conjugate relationship between the two foci, the efficiency of the system is greatly enhanced, because all light emanating from one focus passes through the other, i.e., nothing is lost.

In the practice of the invention, pump light source 30 can be an LED, laser, incandescent light, or any other appropriate source of light capable of inducing fluorescence in a fluorescent material. Wavelength and other characteristics of the pump light are chosen depending on the predetermined chemical to be detected and on the fluorescer-bearing membrane to be used. For example, the pump light may be in the blue but the fluorescence might be in the longer wavelengths, e.g. green or red.

Any of a variety of types of conventional equipment can be used to collect (detect) the fluorescence radiation, as well as information about changes in fluorescence radiation, of the received light in a meaningful format (as an optical signal) from the optical fibers, to provide that information in a meaningful format (as an electrical signal) to the converter, and finally to provide that information, in a meaningful format, to the user of the microbend fiber-optic chemical sensor. Specifically, optical detector 31 can be chosen from known equipment, e.g., photodetector, phototransistor, positive-intrinsic-negative (P-I-N) diode, avalanche photodiode, or photomultiplier.

The optical fibers used in the present invention are formed of any optically transmitting material. Optical quality plastic material, optical quality commercial glass fibers or other conventional fibers can be used. Microbends are easily produced in optical fibers formed of a variety of materials. One type of optical fiber that has been used in the practice of the invention is a 250-$\mu$m diameter plastic optical fiber made of polymethyl methacrylate (PMMA).

There is considerable freedom in the design of the microbends. In order for the invention to function as designed, the length of the microbend section of the optical fiber need be only approximately 1 inch, although it may be longer if so desired. Microbend scattering is basically wavelength-independent, but microbend amplitude is chosen to maximize the fluorescent signal and to provide more efficiency in terms of signal to noise. For a given length of optical fiber, there will be a microbend amplitude that maximizes the strength of the optical power emerging from either end of the fiber. Stated differently, microbend amplitude is chosen to maximize in-scattering. Additionally, microbend amplitudes are not required to be consistent in the different fibers of a single sensor. Structurally speaking, as previously described, in embodiments with multiple fibers, the receiving fibers can be maximized independently of the transmitting fiber, thus providing more flexibility, thus different amplitudes may be chosen for different fibers.

Figure 5:
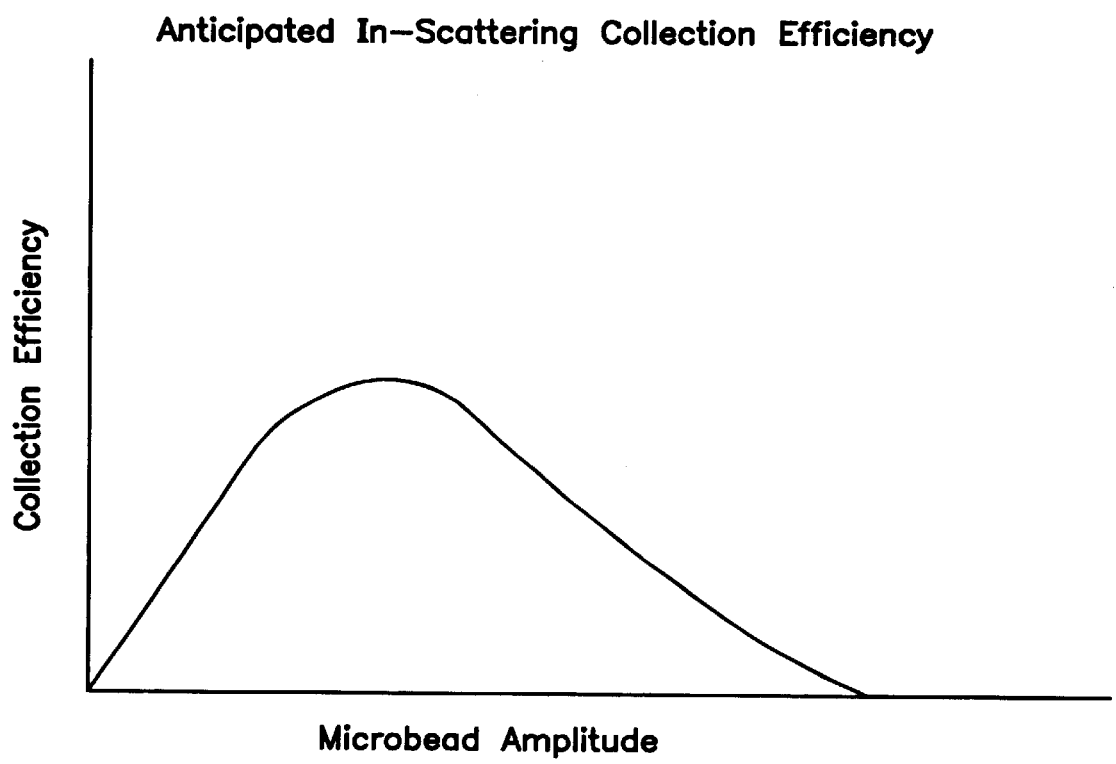
FIG. 5 is a plot of collection efficiency versus microbend amplitude, illustrating the optimum range of amplitude for microbends in the optical fiber axis.

It is important to design the microbend amplitude to conform to the expected needs for the particular sensor embodiment, i.e., the amplitude should not be too large or too small. The optimum amplitude is determined before construction of the sensor. At zero amplitude, no light is scattered into the core, and at a very large amplitude, considerable in-scattering of light occurs, but also out-scattering of some light (as in FIG. 1A) from the fiber occurs before it reaches the straight section. FIG. 5 is a plot of expected collection efficiency versus microbend amplitude as applicable to in-scattering, illustrating that an optimum range of microbend amplitude (at the peak of the curve) can be chosen to maximize the performance features of the microbend fiber-optic chemical sensor, here, in-scattering. Received power first rises rapidly with amplitude, reaches a peak, and gradually diminishes, or approaches some constant, as the amplitude approaches infinity. Generically, choosing microbend amplitudes that are within the amplitude of the incoming light results in more scattering and more light coming out of either end of the optical fiber(s). If the microbend applitude is too big, the sensor can become less efficient at some amplitude because some light will scatter out before traveling the path needed for the sensor to function. If the microbend amplitude is too small, no in-scattering will occur.

Fluorescer-bearing membrane 40 is designed to be selective for the known chemical or chemicals to be identified in the test sample, with a high degree of specificity in order to detect the specific chemical or class of chemicals that the user is looking for. As an example, perylene can be used as the chemically sensitive fluorescent composition of fluorescer-bearing membrane 40. Perylene is a polymer whose fluorescence is significantly reduced when exposed to $NO_2$. Tetraphenyl porphyrin is another polymer that can be used. Its fluorescence is considerably reduced when exposed to $Cl_2$.

Further, fluorescer-bearing membrane 40 can be designed to be selective for more than one known chemical species simultaneously, i.e., in the same test. If used to identify more than one chemical species, results of the detection are separated out after it is detected, using standard optical instrumentation. In sensors using no membrane, spectral analysis may be needed as previously explained. In sensors employing a fluorescer-bearing membrane, where the fiber-optic microbend chemical sensor is to detect more than one chemical species, more than one membrane can be used (if the fluorescence of each membranes is at a different wavelength), with a first membrane designed to be selective for one chemical and to be at least partially transparent to light and a second membrane designed to be selective for a different chemical and to absorb light transmitted through the first membrane. Alternatively, several fluorescers can be used on the same membrane, if the fluorescers are compatible.

Finally, microbend fiber-optic chemical sensor 10 includes, though not shown, the required apparatus (e.g., a microprocessor) and method for converting the detected data relative to intensity (in the case where the analyte is queried directly), changes in fluorescence radiation (such as changed optical power), or shift in fluorescence spectrum analysis to information descriptive of the chemical in the sample being tested. Sensor 10 is pre-calibrated with information about the fluorescence characteristics of the chemical or chemicals expected in the sample. The calibration information is programmed into the equipment for converting the electrical signals from the detector into information about the chemical. Using changes in expected optical power as the indicator, when the detector picks up an optical power change, the signal is converted to information about the expected chemical by comparing the signal with pre-programmed information in the microprocessor. Communication of the information determined about the chemical is accomplished by means of appropriate photodetection equipment and a microprocessor to convert the signal from the detector to the desired information about the chemical. In the absence of a linear relationship between the data obtained by the detector and the calibrated information for quantification of the chemical, a mathematical calculation may be made by the microprocessor to complete the conversion of the signal from the detector to another signal that is descriptive of the chemical.

The present invention has advantages previously unknown in fiber-optic chemical sensors. It improves the efficiency of the fluorescence method of testing samples, e.g., reduced guidance, generation or reduction of fluorescence when pump light is sent through the fiber, and other sensitivity problems. The present invention is easily produced, since the microbends are readily impressed in the fiber because of its relatively low softening point. Additionally, again, the need to strip and re-coat the fiber (i.e., remove and replace the cladding) is eliminated.

Microbend fiber-optic chemical sensor 10 has a wide variety of industrial applications. As a collection device, microbend fiber-optic chemical sensor 10 is useful for industrial processes, environmental monitoring (e.g., smokestack emissions, groundwater, landfills), and detection of gases emanating from materials that are deteriorating in time (e.g., explosives). Microbend fiber-optic chemical sensor 10 has utility in any other applications where it is desirable to determine the presence or amount of a suspected chemical in a liquid or gas.

Although the invention has been described in detail with reference to certain embodiments, the foregoing disclosure, description and drawings herein are only illustrative of particular embodiments of the invention and are not intended to be in any sense limiting. To those skilled in the art to which this invention relates, variations and modifications, different embodiments and applications, of the invention will be obvious from the spirit and scope of the invention, as well as other objects, advantages and features of the invention. All such modifications and equivalents are intended to be covered in the appended claims. The scope of the invention is defined by, and the objects and advantages of the invention may be realized and attained by, the instrumentalities and combinations addressed in the appended claims.

What is claimed is:

1. A microbend fiber-optic chemical sensor for detecting an expected chemical in a chemical-bearing sample, comprising:
   (a) a housing for containing the sample, said housing having a first end and a second end,
   (b) a light source, disposed outside said housing, for generating and providing light to the sample at a wavelength chosen to excite fluorescence,
   (c) an optical fiber means, operably connected to said light source, for guiding light through the sample, said optical fiber means comprising at least one optical fiber, said at least one optical fiber having a microbend section disposed inside said housing and defined by at least one microbend of predetermined amplitude permanently formed in said section, and a straight section disposed outside said housing,
   (d) a means for detecting information about fluorescence radiation returned from the sample, said detecting means being disposed outside said housing and being operably connected to said optical fiber means, and
   (e) a means for converting detected information to information quantifying the chemical in the sample, said converting means being operably connected to said detecting means,
     wherein said light source transmits light along said optical fiber means into said housing, and the light out-scatters from said microbend section into the sample, exciting fluorescence radiation upon contacting the chemical to be detected,
     wherein the fluorescence radiation in-scatters into said microbend section and returns through the sample along said optical fiber means to said detecting means, and
     wherein said detecting means provides information about the fluorescence radiation to said converting means.

2. The microbend fiber-optic chemical sensor, as defined in claim 1, wherein said optical fiber means provides light from said light source directly to the chemical, thereby exciting fluorescence radiation in the chemical, and the intensity of the fluorescence radiation is communicated to said detecting means for conversion to information defining the chemical.

3. The microbend fiber-optic chemical sensor, as defined in claim 1, further comprising a fluorescer-bearing membrane disposed in interactive contact with said microbend section of said optical power means, said membrane comprising at least one fluorescer that reacts with the chemical to be detected, wherein light out-scattered from said microbend section contacts said fluorescer-bearing membrane, exciting fluorescence radiation in said membrane, and wherein, upon contact, the reaction between said fluorescer and the chemical changes the fluorescence radiation, the changes being communicated to said detecting means for conversion to information quantifying the chemical.

4. The microbend fiber-optic chemical sensor, as defined in claim 3, wherein said fluorescer-bearing membrane is a separate structure from said microbend section of said optical fiber means.

5. The microbend fiber-optic chemical sensor, as defined in claim 4, wherein said fluorescer-bearing membrane surrounds said microbend section of said optical fiber means.

6. The microbend fiber-optic chemical sensor, as defined in claim 4, wherein said fluorescer-bearing membrane is formed substantially as a tubular structure having corrugated sides.

7. The microbend fiber-optic chemical sensor, as defined in claim 3, wherein said fluorescer-bearing membrane is coated on said microbend section of said optical fiber means.

8. The microbend fiber-optic chemical sensor, as defined in claim 3, wherein said at least one fluorescer is selected from the group consisting of perylene and tetraphenyl porphyrin.

9. The microbend fiber-optic chemical sensor, as defined in claim 3, wherein the optical power of the fluorescence radiation is quenched, upon contact, by the reaction between said fluorescer and the chemical, and information quantifying the quenching is communicated to said detecting means.

10. The microbend fiber-optic chemical sensor, as defined in claim 3, wherein the optical power of the fluorescence radiation is enhanced, upon contact, by the reaction between said fluorescer and the chemical, and information quantifying the enhancement is communicated to said detecting means.

11. The microbend fiber-optic chemical sensor, as defined in claim 3, wherein the fluorescence radiation undergoes a shift in fluorescence spectrum, upon contact, by the reaction between said fluorescer and the chemical, and information quantifying the spectrum shift is communicated to said detecting means.

12. The microbend fiber-optic chemical sensor, as defined in claim 1, wherein said optical fiber means comprises at least two optical fibers, at least one of said at least two optical fibers for transmitting light through the sample and out-scattering light into the sample, and at least one of said at least two optical fibers for receiving changed, in-scattered light from the sample and returning changed, in-scattered light to the detector, and said at least two optical fibers, and said microbend sections thereof, are spaced apart from, and disposed parallel to, each other.

13. The microbend fiber-optic chemical sensor, as defined in claim 12, wherein said microbend sections of said at least two optical fibers are adjacent.

14. The microbend fiber-optic chemical sensor, as defined in claim 12, wherein said microbend sections of said at least two optical fibers are longitudinally staggered relative to each other.

15. The microbend fiber-optic chemical sensor, as defined in claim 1, further comprising a light-reflecting surface located inside said housing, said surface being operably connected to said optical fiber means, whereby light from said light source being conducted through the sample by said optical fiber means contacts said surface, thereby further out-scattering light into the sample, further in-scattering changed fluorescence radiation into said optical fiber means and further re-directing changed fluorescence radiation to said detecting means.

16. The microbend fiber-optic chemical sensor, as defined in claim 15, wherein said light-reflecting surface is located at said second end of said housing.

17. The microbend fiber-optic chemical sensor, as defined in claim 15, wherein said light-reflecting surface extends lengthwise along the interior of said housing parallel to said optical fiber means.

18. The microbend fiber-optic chemical sensor, as defined in claim 1, further comprising an optical filter located between said microbend section of said optical fiber means and said detecting means, whereby light from said light source conducted through the sample by said optical fiber means is prevented from being detected on return to said detecting means.

19. The microbend fiber-optic chemical sensor, as defined in claim 1, wherein said optical fiber means comprises one optical fiber for transmitting and receiving light, and further comprising a splitter located in said straight section of said optical fiber, whereby said optical fiber is split into two straight sections, a first straight section operably connected to said light source, for transmitting light through the sample along said optical fiber, and a second straight section, operably connected to said detecting means, for returning fluorescence radiation from the sample to said detecting means.

20. The microbend fiber-optic chemical sensor, as defined in claim 1, wherein the sample is gas.

21. The microbend fiber-optic chemical sensor, as defined in claim 1, wherein the sample is liquid.

22. The microbend fiber-optic chemical sensor, as defined in claim 1, wherein the chemical to be detected is an oxide of nitrogen.

23. The microbend fiber-optic chemical sensor, as defined in claim 1, wherein the chemical to be detected is nitrogen dioxide.

24. The microbend fiber-optic chemical sensor, as defined in claim 1, wherein the chemical to be detected is chlorine.

25. The microbend fiber-optic chemical sensor, as defined in claim 1, wherein said housing comprises an inlet port and an outlet port for the sample to pass through.

26. The microbend fiber-optic chemical sensor, as defined in claim 1, wherein said optical fiber means comprises one central transmitting optical fiber for conducting light through the sample and out-scattering light into the sample, and at least two receiving optical fibers, spaced symmetrically around said transmitting optical fiber and substantially parallel thereto, for receiving in-scattered, fluorescence radiation from the sample and returning it to said detecting means.

27. The microbend fiber-optic chemical sensor, as defined in claim 26, further comprising a fluorescer-bearing membrane, formed substantially as a hollow tubular structure having corrugated sides, disposed in interactive contact with said microbend sections of said transmitting optical fiber and receiving optical fibers, said membrane comprising at least one fluorescer that reacts with the chemical to be detected, wherein said at least two receiving optical fibers comprise a plurality of receiving optical fibers, substantially half of said plurality of receiving optical fibers being disposed within said tubular structure and substantially half of said plurality of receiving optical fibers being disposed outside of said tubular structure and within the inward extending curves of the corrugations in said corrugated sides, wherein light out-scattered from said microbend section contacts said fluorescer-bearing membrane, exciting fluorescence radiation in said membrane, and wherein, upon contact, the reaction between said fluorescer and the chemical changes the fluorescence radiation, the changes being communicated to said detecting means for conversion to information quantifying the chemical.

28. The microbend fiber-optic chemical sensor, as defined in claim 3, wherein:

said housing is mirrored internally and formed as a tube having an elliptical shape in cross section, thereby forming an internal ellipse having at least two foci, said optical fiber means comprises at least two optical fibers, at least one fiber for transmitting and out-scattering light, located at one focus of said at least two foci, and at least one fiber for receiving in-scattered, fluorescence radiation from the sample and returning it to said detecting means, located at another focus of said at least two foci, and fluorescer-bearing membrane is coated on said at least one receiving fiber,
whereby all light emanating from one focus of said at least two foci passes through the other.

29. The microbend fiber-optic chemical sensor, as defined in claim 1, further comprising means for pre-calibrating data relative to fluorescence characteristics of the expected chemical in the sample and for programming the calibration data into said converting means, whereby signals indicating fluorescence radiation received by said detecting means are converted to information quantifying the expected chemical by comparing the signals with the programmed information.

30. The microbend fiber-optic chemical sensor, as defined in claim 1, wherein said detecting means comprises a photodetector and said converting means comprises a microprocessor.

31. The microbend fiber-optic chemical sensor, as defined in claim 1, useful for detecting more than one chemical in the sample.

32. A method for detecting an expected chemical in a sample a light source, comprising the steps of:

(a) pre-calibrating a sensing system with data relative to fluorescence characteristics of the expected chemical in the sample, (b) providing the sample to a housing, (c) generating and providing light from a light source to the sample at a wavelength chosen to excite fluorescence, (d) transmitting light through the sample via an optical fiber means comprising at least one optical fiber having a microbend section disposed inside said housing and defined by at least one microbend of predetermined amplitude permanently formed in said section, (e) out-scattering light from the microbend section into the sample, thereby exciting fluorescence radiation upon contact with the chemical to be detected, (f) in-scattering the fluorescence radiation into the microbend section, the fluorescence radiation characteristics of the out-scattered light having been changed by contact with the chemical, (g) receiving the fluorescence radiation from the sample, (h) returning the fluorescence radiation through the sample via the optical fiber means to a detector, (i) detecting optical signals representing the returned fluorescence radiation and the information relative to the changes fluorescence radiation, (j) providing the optical signals from the detector to a converter as electrical signals, and (k) converting the electrical signals to information capable of comparison with the pre-calibrated data, (l) quantifying the chemical in the sample by comparing the converted fluorescence radiation information with the pre-calibrated data.

33. The method of claim 32, wherein the changed fluorescence radiation is detected as intensity indicative of the expected chemical.

34. The method of claim 32, wherein the changes in fluorescence radiation are manifested as changes in optical power in the out-scattered light indicative of the expected chemical.

35. The method of claim 32, wherein the changes in fluorescence radiation are manifested as a shift in the fluorescence spectrum of the out-scattered light indicative of the expected chemical and the detecting step is performed by spectral analysis.

36. The method of claim 32, wherein the converting step further comprises the step of mathematically adjusting the signals from the detector to provide a linear relationship between the signals and the quantification of the chemical.

37. The method of claim 32, comprising the step of programming the calibration data into the converter.

* * * * *